United States Patent [19]
Wiggins et al.

[11] Patent Number: 5,880,222
[45] Date of Patent: Mar. 9, 1999

[54] POLYMERIC THICKENERS FOR AQUEOUS COMPOSITIONS

[75] Inventors: Michael S. Wiggins, Landsdale; Reuben H. Grinstein, Blue Bell, both of Pa.

[73] Assignee: Henkel Corporation, Gulph Mills, Pa.

[21] Appl. No.: 933,708

[22] Filed: Sep. 19, 1997

Related U.S. Application Data

[63] Continuation of Ser. No. 236,328, May 9, 1994, which is a continuation-in-part of Ser. No. 68,344, May 27, 1993, abandoned.

[51] Int. Cl.$^6$ .................................................... C08G 65/32
[52] U.S. Cl. .......................... 525/407; 525/408; 525/409; 525/523; 528/300; 528/408
[58] Field of Search ............................ 524/377; 525/407, 525/408, 409, 523; 528/300, 408

[56] References Cited

U.S. PATENT DOCUMENTS

| | | | |
|---|---|---|---|
| 4,214,101 | 7/1980 | Miya | 562/421 |
| 4,365,024 | 12/1982 | Frentzel | 521/114 |
| 4,419,265 | 12/1983 | Diery | 525/407 |
| 4,420,413 | 12/1983 | Diery | 252/331 |
| 4,440,902 | 4/1984 | Diery | 525/408 |
| 4,687,835 | 8/1987 | Zeilstra | 528/300 |
| 5,019,094 | 5/1991 | Bezwada | 525/408 |
| 5,034,508 | 7/1991 | Nishizaki | 528/408 |
| 5,268,445 | 12/1993 | Gaymans | 528/272 |
| 5,346,959 | 9/1994 | Goman | 525/187 |
| 5,442,016 | 8/1995 | Jarrett | 525/408 |
| 5,522,841 | 6/1996 | Roby | 525/409 |

*Primary Examiner*—Paul R. Michl
*Attorney, Agent, or Firm*—Wayne C. Jaeschke; John Daniel Wood; Henry E. Millson, Jr.

[57] ABSTRACT

Latexes are thickened by compounds of the formula:

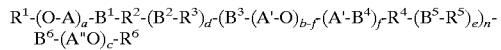

$$R^1\text{-}(O\text{-}A)_a\text{-}B^1\text{-}R^2\text{-}(B^2\text{-}R^3)_d\text{-}(B^3\text{-}(A'\text{-}O)_b\text{-}f(A'\text{-}B^4)_f\text{-}R^4\text{-}(B^5\text{-}R^5)_e)_n\text{-}B^6\text{-}(A''O)_c\text{-}R^6$$

wherein:

$R^1$ and $R^6$ are monovalent hydrophobic groups independently selected from the group consisting of an aliphatic group, a substituted aliphatic group, an aromatic group, and a substituted aromatic group;

$R^2$ and $R^4$ are independently selected from the group consisting of aliphatic, substituted aliphatic, aromatic, or substituted aromatic radicals, each radical being divalent or trivalent;

$R^3$ and $R^5$ are independently selected from hydrogen, lower alkyl and lower aralkyl;

$B^1$, $B^2$, $B^3$, $B^4$, $B^5$, and $B^6$ are linking groups independently selected from the group consisting of an oxygen atom (to form the ether linkage —O—), a carboxylate group (to form an ester linkage $R^2$—C(O)—O— and/or $R^4$—C(O)—O—), an amino group (to form the amine linkage $R^2$—N(R)— and or $R^4$—N(R)—, wherein R is hydrogen, lower alkyl, lower aralkyl, or lower acyl), and an amido group (to form the amide linkage $R^2$—N(R)—C(O)— and/or $R^4$—N(R)—C(O)—, wherein R is hydrogen, lower alkyl, lower aralkyl, or lower acyl);

each of a, b, c, d, e, f, and n are integers, wherein each of a and c are independently any integer from greater than 20 to about 200; b is any integer from greater than 20 to about 450; d, e, and f are zero or 1; and n is any integer from 1 to about 5; and each of A, A', and A" is independently an ethylene, 1,2-propylene, 1,2-butylene unit or combinations thereof.

34 Claims, No Drawings

POLYMERIC THICKENERS FOR AQUEOUS COMPOSITIONS

CROSS-REFERENCE TO RELATED APPLICATIONS

This application is a continuation of U.S. Ser. No. 08/236,328, filed May 9, 1994, which is a continuation-in-part of U.S. Ser. No. 08/068,344, filed May 27, 1993, now abandoned.

FIELD OF THE INVENTION

This invention relates to polymeric compounds which are useful as thickeners for aqueous compositions, especially emulsion polymer latexes.

BACKGROUND ART

Many aqueous systems require thickeners in order to be useful for various types of applications. Such aqueous-based systems as cosmetics, protective coatings for paper and metal, printing inks, and latex paints all require the incorporation of thickeners in order to have the proper rheological characteristics for their particular uses. Many substances useful as thickeners are known in the art. These include natural polymers such as casein and alginates, and synthetic materials such as cellulose derivatives, acrylic polymers, and polyurethane polymers. Polyurethanes have found particular application as latex paint thickeners.

British patent 1,069,735 teaches a process for making water soluble or water swellable surface active products. One aspect of G.B. 1,069,735 teaches that a polymer of the formula R-Y-A-Y-R wherein R is a hydrocarbon radical having more than 8 carbon atoms, Y is the group —NHCOO—, and A is a polyethylene glycol ether by reaction of a polyethylene glycol ether having a molecular weight of at least 1,000 with a monofunctional isocyanate of the formula RNCO wherein R is a hydrocarbon radical having more than 8 carbon atoms. Another aspect of G.B. 1,069,735 teaches that a polymer of the formula R-Y-(A-T)$_n$-A-Y-R wherein R is a hydrocarbon radical having more than 8 carbon atoms, Y is the group —NHCOO—, A is a polyethylene glycol ether, T is a diisocyanate residue, and n is a whole number ≦10 can be made by reaction of a polyethylene glycol ether having a molecular weight of at least 1,000 with a monofunctional isocyanate of the formula RNCO wherein R is a hydrocarbon radical having more than 8 carbon atoms. A third aspect taught by G.B. 1,069,735 is that a polymer of the formula R-X-(A-T)$_n$-A-X-R wherein R is a hydrocarbon radical having more than 8 carbon atoms; x is the group —NHCOO—, —SCONH—, —NHCONH—,) N—CONH—, or —CONH—; A is a polyethylene glycol ether, T is the diisocyanate residue, and n is a whole number ≦10 by reaction of a polyethylene glycol ether having a molecular weight of at least 1,000 and a diisocyanate so that an excess of isocyanate groups is present over those needed to react with the hydroxyl groups of the polyethylene glycol and a monofunctional alcohol, mercaptan, phenol, or carboxylic acid or a primary or secondary amine, said monofunctional compound has a hydrocarbon radical having more than 8 carbon atoms; in which process the total amount of hydrocarbon radical which contains more than 8 carbon atoms does not amount to>6% by weight of the reaction product. Japanese Kokai Patent 48-97783 teaches that compounds of the formula

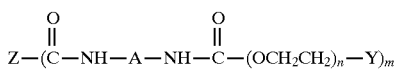

wherein Z is a polyether polyol residue derived from a compound containing active hydrogen atoms and alkylene oxide in which the polyether contains 20%–90% by weight oxyethylene groups; m is a number ranging from 2 to 8 and which signifies the number of hydroxyl groups per polyether polyol molecule; A is the residue of a divalent organic group such as a tolylene diisocyanate residue; Y is a residue of a compound containing active hydrogen atoms such as an ethoxylated $C_{14}$ aliphatic alcohol; and n is a number equal to at least 3, can be used as thickeners in aqueous media such as in latex paints. U.S. Pat. No. 4,079,028 teaches a latex paint composition containing an emulsion polymer and from 0.1 to about 10% by weight based on emulsion polymer solids of a thickener selected from polymers of Groups A, B, and C. Polymers of group A are linear polymers of the formula A-B$_p$-E$_q$-(B-E)$_m$-B$_r$-E$_t$-A wherein each of p, q, r, and t independently is zero or 1; at least one of q and r is 1, and t is zero when r is zero; provided that, when q is 1, then: (a) each of p, r, and t is zero; or (b) p is zero and each of r and t is 1; or (c) t is zero and each of r and p is 1; and when q is zero, then r is 1 and each of p and t is zero; A is a hydrophobic organic radical containing at least one carbon atom; B is a divalent hydrophobic group of the structure

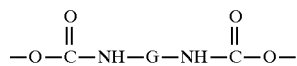

where G is the residue of an organic di- or triisocyanate; E is a divalent, hydrophilic, nonionic polyether groups of molecular weight of at least about 1,500 and m is at least 1. Polymers of group B are designated as star-shaped products of the formula [H-E-OCH$_2$]$_s$L[Q$_v$-(D$_u$-E-A)$_w$R$_z$]$_m$ where L is X, Y or —O—, Q is —CH$_2$C≡, D is —CH$_2$O—, m is 2–4, s is zero to 2, the sum of m and s is the valence of L, w is 1–3, and each of u and z independently is zero or 1; and where X is a hydrocarbon radical containing at least 1 carbon atom, preferably 1–4 carbon atoms; and Y is a trivalent radical selected from —OCONH(CH$_2$)$_6$N[CONH (CH$_2$)$_6$NHCO—O]$_2$—, CH$_3$C[CH$_2$—O—OCNHC$_7$H$_6$NHCO]$_3$—, and CH$_3$CH$_2$C[CH$_2$—O—OCNHC$_7$H$_6$NHCO]$_3$— provided that: (a) when L is X, then u and w are each 1, v and z are each zero, the sum of m and s is 4, and m is at least 2; (b) when L is Y, then u, v and s are each zero, m is 3, w is 2–3, and z is zero or 1; (c) when L is —O—, then v and u are each 1, m is 2, w is 1–3, and each of s and z is zero. Polymers of group c are complex mixtures of linear, branched, and sub-branched products which form networks or hydrophobes and hydrophobic segments interspersed with hydrophilic segments. The essential elements of these polymers are a polyfunctional compound containing at least 3 hydroxyl or isocyanate groups, a difunctional compound reactive with the polyfunctional compound, and a monofunctional reactant such as a monohydroxy or monoamino compound. U.S. Pat. No. 4,155,892 teaches a composition consisting essentially of water and an amount of a thickener polymer selected from the polymers disclosed in U.S. Pat. No. 4,079,028 above to thicken the water. U.S. Pat. No. 4,499,233 teaches a water dispersable modified polyurethane which is the product of the reaction of: (a) a polyisocyanate; (b) a polyether polyol; (c) a modifying agent which is a multifunctional compound such as α,ω-amino alkanes and aromatic diamines such as 1,4-diaminobenzene; and (d) a capping agent such as a monoisocyanate. U.S. Pat. No. 4,499,233 also teaches a thickened aqueous composition comprised of water and from about 0.005 to about 10.00% by weight of a water dispersable modified polyurethane as disclosed above.

U.S. Pat. No. 4,426,485 teaches thickeners for aqueous systems which are water-soluble polymers having a molecular weight of at least 10,000 and which are comprised of hydrophobic segments each containing at least one monovalent hydrophobic group covalently bonded to the polymer. At least one of the hydrophobic segments has at least two hydrophobes thereby forming a bunch of hydrophobes within the hydrophobic segment. The hydrophobes within a bunched hydrophobic segment are in close association when they are separated by no more than about 50 covalently bonded, sequentially connected atoms. One example of such a polymer is made by reacting a polyurethane pre-polymer comprised of PEG 8000 and toluene diisocyanate with toluene diisocyanate and the diol formed by reaction of epichlorohydrin and a 10 mole ethylene oxide adduct of nonyl phenol.

A non-urethane thickener is disclosed in U.S. Pat. No. 3,770,684 which teaches latex compositions containing from about 0.1% to about 3.0% of a compound of the general formula R-X-(water soluble polyether)-X-R' wherein R and R' are water insoluble hydrocarbon residues; X is a connecting linkage selected from the group consisting of an ether linkage, an ester linkage, an amide linkage, an imino linkage, a urethane linkage, an sulfide linkage, or a siloxane linkage. U.S. Pat. No. 3,770,684 also teaches that the preferred water soluble polyether is a polyethylene oxide polymer having a molecular weight of from 3,000 to 35,000 or an ethylene oxide-propylene oxide copolymer having a molecular weight of from 3,000 to 35,000.

SUMMARY OF THE INVENTION

This invention relates to compounds which are useful as thickeners for aqueous compositions, particularly latex paints, which compounds have the formula I:

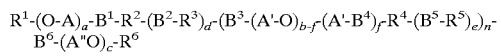

$R^1$-(O-A)$_a$-B$^1$-R$^2$-(B$^2$-R$^3$)$_d$-(B$^3$-(A'-O)$_b$-$_f$(A'-B$^4$)$_f$-R$^4$-(B$^5$-R$^5$)$_e$)$_n$-B$^6$-(A"O)$_c$-R$^6$ wherein:

$R^1$ and $R^6$ are monovalent hydrophobic groups independently selected from the group consisting of an aliphatic group, a substituted aliphatic group, an aromatic group, and a substituted aromatic group;

$R^2$ and $R^4$ are independently selected from the group consisting of aliphatic, substituted aliphatic, aromatic, or substituted aromatic radicals, each radical being divalent or trivalent;

$R^3$ and $R^5$ are independently selected from hydrogen, lower alkyl and lower aralkyl;

$B^1$, $B^2$, $B^3$, $B^4$, $B^5$, and $B^6$ are linking groups independently selected from the group consisting of an oxygen atom (to form the ether linkage —O—), a carboxylate group (to form an ester linkage $R^2$—C(O)—O— and/or $R^4$—C(O)—O—), an amino group (to form the amine linkage $R^2$—N(R)— and or $R^4$—N(R)—, wherein R is hydrogen, lower alkyl, lower aralkyl, or lower acyl), and an amido group (to form the amide linkage $R^2$—N(R)—C(O)— and/or $R^4$—N(R)—C(O)—, wherein R is hydrogen, lower alkyl, lower aralkyl, or lower acyl);

each of a, b, c, d, e, f, and n are integers, wherein each of a and c are independently any integer from greater than 20 to about 200; b is any integer from greater than 20 to about 450; d, e, and f are zero or 1; and n is any integer from 1 to about 5; and each of A, A', and A" is independently an ethylene, 1,2-propylene, 1,2-butylene unit or combinations thereof.

In preferred compounds, each of $R^1$ and $R^6$ is independently an aliphatic, substituted aliphatic, aromatic, or substituted aromatic radical having from 4 to about 50 carbon atoms; each of $B^1$–$B^6$ is an oxygen atom; $R^2$ and $R^4$ are both either propanetriyl or meta-xylyl; d and e are either (i) both zero (e.g. when $R^2$ and $R^4$ are both meta-xylyl) or (ii) both 1 and $R^3$ and $R^5$ are hydrogen, methyl or benzyl (e.g. when $R^2$ and $R^4$ are both propanetriyl); f is zero; each of A, A', and A" are ethylene, n is 1, b is from about 50 to about 450, more preferably from about 90 to about 450, and the values of a and c independently range from about 50 to about 150.

This invention relates to a thickened aqueous composition comprised of water and a thickening-effective amount of one or more of a compound of the formula I and also relates to a latex composition comprising an emulsion polymer and from about 0.1 to about 20 percent by weight based on emulsion polymer solids of a compound of the formula I.

DETAILED DESCRIPTION OF THE PREFERRED EMBODIMENTS

In regard to formula I, the abbreviations A, A', and A" stand for the ethylene group (—CH$_2$CH$_2$—), the 1,2-propylene group —(CH$_2$CH(CH$_3$)—), or the 1,2-butylene group (—CH(CH$_2$CH$_3$)CH$_2$—) or combinations thereof. Each of the subscripts a, b, c, f, and n are independently any integer as set forth above. One of ordinary skill in the art will appreciate that for mixtures of pure compounds, the subscripts a, b, c, f, and n will have non-integer values to reflect the fact that they represent the average degree of polymerization, e.g. n is from 0.5 to 4.5, preferably 0.5 to 1.5.

$R^2$ and $R^4$ are aliphatic, substituted aliphatic, aromatic, or substituted aromatic radical having a valence of from 2 or 3. Such aliphatic radicals include any di- or trivalent: (a) straight chain and branched alkyl radicals having from 2 to about 50 carbon atoms (preferably divalent or trivalent alkylene radicals having from 2 to 10 carbon atoms); (b) cycloalkyl radicals having from 4 to about 20 carbon atoms; (c) straight chain and branched alkenyl radicals having from 2 to about 40 carbon atoms; (d) cycloalkenyl radicals having from 5 to about 20 carbon atoms; (e) straight chain and branched alkynyl radicals having from 2 to about 30 carbon atoms; cycloalkynyl radicals having from 6 to about 20 carbon atoms; and (f) aralkyl radicals (i.e. alkyl radicals having aromatic groups as pendent substituents or linking alkylene groups) having at least 2 aliphatic carbon atoms along with an aromatic group, e.g. meta-xylyl wherein methylene groups are linked by a benzenoid group). Aliphatic radicals also include those above-mentioned aliphatic radicals which contain one or more heteroatoms substituted for one or more hydrogen atoms. The heteroatoms include the halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like. For purposes of this invention, it is understood that aliphatic includes cycloaliphatic and heterocycloaliphatic wherein the heteroatoms are nitrogen, oxygen, sulfur, and phosphorus.

An aromatic radical is any benzenoid or non-benzenoid aromatic radical having a valence of 2 to 8. A non-benzenoid aromatic radical includes carbocyclic and heterocyclic aromatic radicals. For purposes of this invention, a substituted aromatic radical is any benzenoid or non-benzenoid aromatic radical having a valence of from 2 to 6 wherein one or more hydrogen atoms is replaced by an atom or a group of atoms other than hydrogen including the halogens, nitrogen, sulfur, oxygen, and phosphorus or groups of heteroatoms such as nitro, sulfonic acid, $C_{1-10}$ alkyl sulfonate ester, sulfoxide, sulfone, phosphoryl, trihalomethyl, and the like.

The abbreviations NP, DNP, LA, and TD stand for nonylphenoxy, dinonylphenoxy, lauryl, and tridecyl, respectively. $R^1$ and $R^6$ are monovalent radicals, typically having from about 6 to about 50 carbon atoms. The use of a hydrophobic alcohol to form the ends of the compound of formula I described above results in the formation of hydrophobic ether residues as $R^1$ and $R^6$. A hydrophobic group is any group which contributes to the water insolubility of the ether residue. Unsubstituted aliphatic groups having at least 6 carbon atoms, aromatic groups having 6 or more carbon atoms and groups which contain both aliphatic and aromatic moieties are hydrophobic. Examples of useful hydrophobic ether residues include but are not limited to, tolyl, hexyl, ethylphenyls, heptyl, cumyl, propylphenyls, octyl, butylphenyls, nonyl, phenylphenyls, pentylphenyls, decyl, isohexylphenyls, n-hexylphenyls, n-undecyl, heptylphenyls, lauryl, octylphenyls, isononylphenyls, n-nonylphenyls, tetradecyl, decylphenyls, n-undecylphenyls, hexadecyl, isododecylphenyls, n-dodecylphenyls, stearyl, n-tetradecylphenyls, hexadecylphenyls, and isooctadecylphenyls. Preferred hydrophobes are the nonylphenyl, dinonylphenyl, lauryl, and tridecyl groups.

The use of the term "lower" to modify "alkyl" shall mean an alkyl group having from 1 to about 4 carbon atoms, e.g. methyl, ethyl, n-propyl, isopropyl, and tert-butyl. Further, the term "lower" when used to modify "aralkyl" shall mean an alkyl group having from 1 to about 4 carbon atoms substituted with a benzenoid radical, and the term "lower" when used to modify "acyl" shall mean a carbonyl terminated lower alkyl or lower aralkyl radical.

Each of A, A', and A" groups of formula I represent an ethylene, 1,2-propylene, 1,2-butylene unit or combinations thereof such that each of $(A-O)_a$, $(A'-O)_b$ and $(A"-O)_c$ is a water soluble, or water dispersable polyether group. The water solubility or water dispersability of a polyether group is a function of its molecular structure and/or its molecular weight. For example, an ethyleneoxy (EO) homopolymer having a molecular weight of about 20,000 daltons or less is water soluble while a water soluble propyleneoxy (PO) homopolymer has a molecular weight of less than about 700 daltons. The structure of an EO–PO copolymer must be such that it contains at least about 50 wt % of ethyloxy groups to be water soluble. The structure-property relationships of EO and PO polyethers is described in the *Encyclopedia of Polymer Science and Engineering*, Second Edition, vol. 6, pp. 225–273, (John Wiley and Sons, Inc, 1986), while those of poly PO are described in vol. 6, page 300. In preferred compounds, the A, A', and A" groups consist essentially of ethylene groups, the value of b in formula I above is preferably from about 50 to about 450, more preferably from about 90 to about 450, and the values of a and c preferably range from about 50 to about 150.

The compounds according to the invention are polymeric materials which can be made by any process within the purview of those having ordinary skill in the art. A preferred method is a two-step process, the first step of which comprises forming a mixture of compounds of the following formulas:

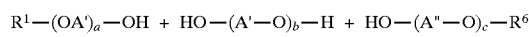

$$R^1-(OA')_a-OH + HO-(A'-O)_b-H + HO-(A''-O)_c-R^6$$

$$\text{II} \quad\quad\quad \text{III} \quad\quad\quad \text{IV}$$

wherein all symbols are as set forth above and under conditions which cause at least a portion of the terminal hydrogen atoms of the hydroxyl groups shown above to ionize leaving alkoxide oxygen atoms. These conditions can be brought about by adding to the mixture a strong base, for example an alkali or alkaline earth metal lower alkyl alkoxide, e.g. sodium methoxide. Of course, when B is an amino or amido group, the terminal hydroxyl of the compounds of formulas I, II, and III should be replaced by an amine nitrogen having the appropriate substituents to introduce the desired B and R groups into the molecule. Examples of such amine functional compounds useful to introduce an amine group are the polyoxyethyleneamine and polyoxypropyleneamines (available under the tradename Jeffamine, from Texaco Chemical Company, Houston, Tex.). Compounds of formula II and IV, but wherein the terminal hydroxy is replaced by an amino nitrogen can be prepared by one of ordinary skill in the art. For example, compounds of formula II and IV can be subjected to a catalyzed ammoniation (with ammonia, or a lower alkylamine or lower acyl amide) for replacement of the hydroxyl, or to a capping of the hydroxyl with epichlorohydrin followed by ammoniation (with ammonia, or a lower alkylamine or lower acylamide) of the resulting glycidal group.

The second step of the two-step process comprises forming a mixture of the product of step one in further admixture with a member selected from the group of a di-etherifying agent, a tri-etherifying agent, a di-esterifying agent, a tri-esterifying agent, and a mixture of two or more of such members. (Of course, when the compounds are amines or amides rather than hydroxyl compounds, the reaction is an alkylation or amidation reaction. To simplify the following description, references below to etherifying agents or esterifying agents in general should be construed as applicable to alkylating agents and amidifying agents, respectively.) This basic reaction can be represented by:

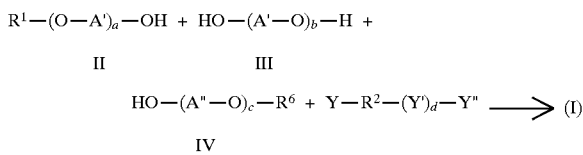

$$R^1-(O-A')_a-OH + HO-(A'-O)_b-H +$$

$$\text{II} \quad\quad\quad \text{III}$$

$$HO-(A''-O)_c-R^6 + Y-R^2-(Y')_d-Y'' \longrightarrow \text{(I)}$$

$$\text{IV}$$

wherein Y, Y' and Y" are leaving groups in the case of etherifying agents or carboxy-functional groups in the case of esterifying agents. (Of course, the hydroxyl groups of the compounds of formulas II, III, and IV are amino or amido groups when B is to be such a linking group. Further, $Y-R^2-(Y')_d-Y''$ can also be an acetal, ketal, or orthoester, in which case Y and Y" are lower alkoxy groups which leave in a transacetalization, transketalization, or transorthoesterification, respectively. This leads to a compound of formula I in which B is an ether linking group from these special classes of ethers, i.e. acetals, ketals or orthoesters.)

It should be noted that when all B linkages are to be, for example, ether linkages, then only a di-etherifying agent and/or a tri-etherifying agent will be used to the exclusion of any esterifying agents. Likewise, when all B linkages are to be ester linkages, then only a di-esterifying agent and/or a tri-esterifying agent will be used to the exclusion of any etherifying agents. Similarly, if both d and e are to be zero (i.e. $R^2$ and $R^4$ are only divalent radicals), then only a di-etherifying agent and/or a di-esterifying agent will be used to the exclusion of any tri-etherifying agents and tri-esterifying agents. Such etherifying (or alkylating) and esterifying (or amidifying) agents are capable of reacting with the hydroxyl (or amine or amide groups) or alkoxide oxygens of the reactants II, III and IV, above. These agents will thus introduce the divalent or trivalent radicals $R^2$ and $R^4$ into the molecule. Examples of etherifying (or alkylating) agents are alkyl halides, e.g. divalent compounds (e.g. alpha,alpha'-dichloro-meta-xylene) that introduce a divalent $R^2$ and/or $R^4$ group into the molecule, e.g. through the same mechanism as a classical Williamson ether (or amine alkylation) synthesis. When $R^2$ and/or $R^4$ are to be aromatic radicals, it may be convenient to employ a di-halo-aromatic compound (e.g. di-bromo-benzene) which can be derivatized to the corresponding mono-Grignard reagent and reacted with the diol reactant of formula III, above (which will cap the diol with ether groups $R^2$ and/or $R^4$ at each end of the diol to form, in the case of di-bromo-benzene, a bis-bromo-phenyl ether of the diol). This capped adduct can then be sequentially derivatized in a second Grignard reaction, the product of which can be reacted with reactants of formulas II, and IV, above, to give a compound of formula I wherein $R^2$ and/or $R^4$ are aromatic groups.

Further examples of etherifying agents include epihalohydrin compounds, (e.g. those of the formula X—$CH_2$—CH—(O)—$CH_2$ wherein X is a leaving group, for example a halogen, e.g. chlorine which forms a chloride ion as the leaving group) or a precursor of an epihalohydrin (e.g. a compound of the formula X—$CH_2$—CH—($OR^3$)—$CH_2$—X', wherein X' is a leaving group). When this precursor is used, the epihalohydrin, may be formed, at least in part, in situ, or the alkoxide moieties formed in step one may displace both the X and X' groups in an $S_N2$ reaction. When $R^3$ and/or $R^5$ are lower alkyl, then the epihalohydrin compound may be an ether having the formula X—$CH_2$—CH—($OR^3$)—$CH_2$—X', wherein X and X" are leaving groups and $R^3$ is a lower alkyl group (i.e. $C_1$ to $C_4$ alkyl, preferably methyl). Alternatively, the reaction mixture may also contain an alkylating agent of the formula X"-$R^3$ (e.g methyl chloride or benzyl chloride) that can react with the alkoxide radical (or hydroxyl group) formed by opening of the oxirane ring of the epihalohydrin. This alkylating agent would preferably be added with the epihalohydrin compound to reduce the opportunity of a side reaction with the alkoxide compounds which introduce the $R^1$ and $R^6$ groups into the molecule. Of course, if $R^3$ and $R^5$ are different, then a second epihalohydrin ether having the formula X—$CH_2$—CH—($OR^5$)—$CH_2$—X' and/or a second alkylating agent having the formula X"-$R^5$ must be employed to introduce the $R^5$ group into the molecule.

Examples of esterifying agents include di-basic and tri-basic organic acids, and reactive derivatives thereof, e.g. acid halides, acid anhydrides, and/or lower esters of such di-basic and tri-basic organic acids (all of which have carboxy-functional groups capable of reacting with the hydroxyl or alkoxide functional compounds of formulas II, III, IV). Because branching is generally undesirable (as discussed below in the context of the epihalohydrin etherifying agents), if an esterifying agent is employed, it is preferably only di-basic, e.g. succinic acid or phthalic anhydride. If a tri-basic acid is employed, a lower alkanol (e.g. methanol) can be added to the reaction mixture so that $R^3$ and/or $R^5$ will be lower alkyl. (This addition of a lower alkanol is similar to the chain stopping effect discussed below in the context of alkyl halides used with epihalohydrins). The reaction conditions for the esterification reaction will of course differ from those appropriate for an etherification reaction. Esterification reactions with polybasic acids are discussed in the *Encyclopedia of Polymer Science and Engineering*, vol. 12, pp. 28–43 (John Wiley and Sons, Inc, New York, N.Y., 1988), the disclosure of which is incorporated herein by reference. The presence of ester linkages is less desirable when the compound will be used in aqueous compositions that are not at an essentially neutral pH (e.g. from a pH of about 6.5 to about 7.5) Because many latex compositions are formulated to have an alkaline pH (e.g. about pH 9 to about pH 11), compounds of formula I wherein all B linkages are ether linkages are preferred for their resistance to hydrolysis.

The ratios of the reactants of formulas II, III, and, IV may vary, but will generally range within 20 mole % to 45 mole % each of the compounds of formula II and IV (if $R^1$ and $R^6$ are the same, then the amount of the single reactant will, thus, be 40 mole % to 90 mole %) and 3 mole % to 60 mole %, preferably 10 mole % to 60 mole %, of the compound of formula III. The amount of the etherifying or esterifying compound that is then reacted with the alkoxides may also vary, but will generally range from about 0.25:1 to about 1.5:1.0 (preferably about 0.8:1 to 1.2:1) equivalents of etherifying agent or esterifying agent (a divalent agent having two equivalents per mole) to hydroxyl equivalent weights of the reactants of formulas II (having one equivalent per mole), III (having two equivalents per mole), and IV (having one equivalent per mole).

It is believed that compositions which contain predominantly compounds of formula I are superior thickeners compared to compositions which contain compounds wherein $R^3$ and/or $R^5$ are not hydrogen, lower alkyl, or lower aralkyl, but are larger organic groups. Such larger organic groups can result from the reaction of a second molecule of epichlorohydrin with, e.g., the intermediate alkoxide compound of the formula:

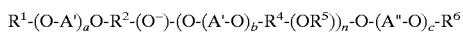

$R^1\text{-}(O\text{-}A')_a O\text{-}R^2\text{-}(O^-)\text{-}(O\text{-}(A'\text{-}O)_b\text{-}R^4\text{-}(OR^5))_n\text{-}O\text{-}(A''\text{-}O)_c\text{-}R^6$ and that this second molecule of epichhlorohydrin can react, or may already have reacted, with the alkoxide $R^1$-$(O$-$A')_a$-$O^-$ (or $R^6$-$(O$-$A'')_c$-$O^-$). In this case, a compound will be formed which has a similar structure to the compounds of formula I, but in which $R^3$ will then have the formula:

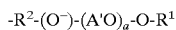

$\text{-}R^2\text{-}(O^-)\text{-}(A'O)_a\text{-}O\text{-}R^1$ which yields a molecule with significant branching in its molecular structure. Of course, such branching can also occur at $R^4$ wherein $R^5$ is similarly replaced by the reaction product of a second molecule of epichlorohydrin and an alkoxide. (If a tri-esterifying agent is use, then the branching will result from reaction of the third carboxyl group with one of the reactants of formulas II, III, and IV.) This branching is believed to be detrimental to the performance of the molecule as a thickener for latex compositions. Thus, techniques to reduce this branching and produce compositions comprised predominantly of compounds of formula I should be employed in preparing the compounds of this invention.

Techniques to reduce branching include maintaining a comparatively low concentration of free epichlorohydrin in the reaction mixture. This can be done by using less than the stoichiometric amount of epichlorohydrin or by slow addition of the stoichiometric amount of epichlorohydrin. In the former case, there will be excess alkoxide present that should be recovered and recycled to maintain an efficient production process. In the latter case, slow addition of the epichlorohydrin will reduce the rate of product throughput in the reactor vessel.

Another useful technique is to introduce a reactant which will compete with the epichlorohydrin in the branching reaction. For example, water or an alkylating agent can react with the alkoxide group of the intermediate alkoxide compound set forth above. If water reacts with the alkoxide intermediate, branching is inhibited because the alcohol group is not as reactive with free epichlorohydrin as the alkoxide group of the alkoxide intermediate. Typical concentrations of water in the reaction medium range from 100 ppm to 2000 ppm water in the reaction solvent. If a lower alkyl alkylating agent reacts with the alkoxide intermediate, the alkoxide is capped with a lower alkyl group, thus preventing reaction (i.e. a sort of chain stopping effect) with free epichlorohydrin or the reaction product of epichlorohydrin with the hydrophobe alkoxide $R^1$-(O-A')$_a$-O$^-$ and/or $R^6$-(O-A")$_c$-O$^-$.

Aqueous compositions comprised of thickeners according to the invention are also part of the invention. These compositions are comprised of water and a thickening-effective amount of one or more compounds of formula I. A thickening-effective amount is any amount required to bring the viscosity of the aqueous composition within the range desired for the intended application, e.g. a Brookfield viscosity of from about 3,000 to about 5,000 cps (spindle #3, @ 30 r.p.m.). This amount will typically be from about 1 to about 50% by weight of compounds according to the invention. An aqueous composition according to the invention may also be comprised of from about 1 to about 50% by weight of one or more compounds according to the invention, and, optionally, from about 1% to about 30% by weight of a viscosity modifier which is a compound selected from the group consisting of a liquid polyol, a liquid ethoxylated or propoxylated $C_{1-8}$ alcohol, or a liquid ethoxylated or propoxylated $C_{1-8}$ carboxylic acid. A liquid polyol is any compound having two or more —OH groups which is a liquid at room temperature, examples of which include but are not limited to ethylene glycol, 1,2-propylene glycol, 1,3-propylene glycol, 1,2-butylene glycol. A liquid ethoxylated or propoxylated $C_{1-8}$ alcohol is any aliphatic alcohol ethoxylated or propoxylated to any degree of ethoxylation or propoxylation and which is a liquid. Compounds in which the —OH group of the liquid ethoxylated or propoxylated $C_{1-8}$ alcohol is etherified with a $C_{1-4}$ alkyl group are also included in this group. A liquid ethoxylated or propoxylated $C_{1-8}$ carboxylic acid is any aliphatic carboxylic acid ethoxylated or propoxylated to any degree of ethoxylation or propoxylation and which is a liquid. Preferred viscosity modifiers include butoxy triglycol (triethylene glycol monobutyl ether), butyl carbitol (diethylene glycol monobutyl ether), or 1,2-propylene glycol. Also preferred are combinations of butoxy triglycol, butyl carbitol, and 1,2-propylene glycol which total from about 1% to about 30% by weight of the total composition. An aqueous composition will typically contain about 40% by weight of water, about 40% by weight of a thickener according to the invention and about 20% by weight of one or a combination of butoxy triglycol, butyl carbitol and 1,2-propylene glycol. The preferred composition is comprised of about 40% by weight of water, about 40% by weight of a thickener according to the invention and about 20% by weight of butoxy triglycol.

The thickeners according to the invention also afford commercial thickener products which have important economic and practical advantages over conventional thickener products because they contain significantly greater amounts of thickener per unit weight of product. For example, typical commercial thickeners are aqueous compositions containing from about 20% to about 30% by weight thickener and having a Brookfield viscosity of about 15,000 cps. Thickener products containing thickeners according to the invention can be sold commercially as aqueous-based compositions containing from about 35% to about 40% by weight thickener and having Brookfield viscosities ranging from about 400–20,000 cps. The thickeners according to the invention afford commercial products which are higher in solids and are easier to handle because of their lower viscosities.

The thickeners according to the invention are very efficient in increasing the high shear and low shear viscosities of latexes or latex paint compositions into which they have been incorporated. Latexes are emulsions or dispersions of water insoluble polymers in water. Latex paint compositions typically contain at least an aqueous emulsion or dispersion of a water insoluble polymer, a pigment, a pigment dispersant, a thickener to control the viscosity and improve the leveling and flow characteristics of the paint, and a preservative which is effective in controlling the growth of microorganisms. Present paint industry standards call for a latex paint having an ICI viscosity of from about 0.8 to about 3.0 poise and a Stormer viscosity of from about 90 to about 110 KU. The ICI viscosity is a high shear viscosity and is measured on the ICI (Research Equipment Limited) Cone and Plate Viscosimeter at a shear rate of about 10,000 sec$^{-1}$. The Stormer viscosity is given in Krebs Units (KU) and is measured according to ASTM D662-81. Examples of the latexes which can be thickened with the thickeners according to the invention are those disclosed in U.S. Pat. No. 4,079,028 at column 12, line 64, to column 14, line 7, the entire contents of which are incorporated herein by reference.

The thickening ability of the compounds according to the invention can vary with the type of substance to be thickened. For example, some compounds may be very efficient at thickening acrylic latexes and not as efficient at thickening styrene-acrylic latexes while others may exhibit the opposite behavior. In addition, the thickening ability of a particular compound may also change when that compound is used in a paint formulation as opposed to a composition comprising only latex and water.

For most commercial applications, a latex is thickened by adding a sufficient amount of an aqueous composition according to the invention to a latex to bring the ICI viscosity into the 0.8 to 3.0 poise range and the Stormer viscosity into the 95 to 105 KU. Typically this amount will be in the range of from about 0.1% to about 10% of the thickener according to the invention by weight of latex polymer solids and preferably between 1% and 3% by weight of latex polymer solids. The following examples are meant to illustrate, but not limit, the invention. U.S. Ser. No. 07/787,905, filed Nov. 7, 1991, discloses related materials and methods, the entire disclosure of which application is incorporated herein by reference.

EXAMPLES

Example 1

This example will illustrate the use of dimethyl benzyl acetal to introduce the tolyl group into the structure of the molecule. To a 250 ml round bottom flask equipped with a stirrer, nitrogen inlet tube, and a distillation head were added 80 millimoles of nonylphenol ethoxylate (nominal 100 ethyleneoxy units per mole of ethoxylate) and 20 millimoles of polyethylene glycol having a molecular weight of about 8,000 grams/mole and sufficient toluene to form a dilute solution/dispersion. The mixture was heated to azeotropically distill off moisture in the reactants with stirring+$N_2$ sparge. After the water concentration is reduced, e.g to less than 50 ppm the mixture was cooled to 80° C. Benzyl dimethyl acetal in an amount of 60 millimoles was then added and heat was applied to distill off formed methanol. The remaining toluene was then vacuum distilled off. Butoxytriglycol (BTG) and water were then added.

Example 2

This example will illustrate the production of a compound of formula I wherein $B^3$ and $B^4$ are amino groups. To a round bottom flask equipped with a stirrer, nitrogen inlet tube, and a distillation head, add 80 millimoles of nonylphenol ethoxylate (nominal 100 ethyleneoxy units per mole of ethoxylate) and 400 grams of toluene. To this mixture, add 80 millimoles of sodium hydroxide (as an aqueous solution at 50% by weight sodium hydroxide). Then heat the flask to azeotropically distill off most of the water with stirring and nitrogen gas sparging. Cool the solution to 80° C. after which add 80 millimoles of epichlorohydrin. Allow to react until substantially all of the nonylphenol ethoxylate is capped with epichlorohydrin. Then add 20 millimoles of a polyethylene glycol having a molecular weight of about 6,000 grams/mole and amine terminated at each end (e.g. Jeffamine ED-6000). The reaction mixture is then maintained at 120° C. until the epoxide titration reaches approximately zero. (A 4.0 gram aliquot of the reaction mixture+4 grams of tetraethylammonium bromide can be dissolved in 50 ml of glacial acetic acid and the resulting solution titrated with a 0.1036N $HClO_4$ in glacial acetic acid solution to a methyl violet end point for the amount of epoxide (epoxy titration). The reaction mixture can then be neutralized to a substantially neutral pH (about pH 7) with aqueous hydrochloric acid. Butoxytriglycol (BTG) and water can then be added.

Example 3

This example will illustrate the production of a compound of formula I wherein $B^3$ and $B^4$ are amido groups. To a round bottom flask equipped with a stirrer, nitrogen inlet tube, and a distillation head, add 80 millimoles of nonylphenol ethoxylate (nominal 100 ethyleneoxy units per mole of ethoxylate) and 400 grams of toluene. To this mixture, add 80 millimoles of sodium hydroxide (as an aqueous solution at 50% by weight sodium hydroxide). Then heat the flask to azeotropically distill off most of the water with stirring and nitrogen gas sparging. Cool the solution to 80° C. after which add 80 millimoles of chloroacetic acid. Allow to react until substantially all of the nonylphenol ethoxylate is capped. Then add 20 millimoles of a polyethylene glycol having a molecular weight of about 6,000 grams/mole and amine terminated at each end (e.g. Jeffamine ED-6000). The reaction mixture is then maintained at 120° C. until the reaction reaches substantial completion. The reaction mixture can then be neutralized to a substantially neutral pH (about pH 7) with aqueous hydrochloric acid. Butoxytriglycol (BTG) and water can then be added.

Example 4

This example illustrates the production of a compound of formula I wherein $B^3$ and $B^4$ are ether linkages. To a round bottom flask equipped with a stirrer, nitrogen inlet tube, and a distillation head, were added 70 millimoles of tridecyl alcohol ethoxylate (nominal 100 ethyleneoxy units per mole of ethoxylate), 30 millimoles of polyethylene glycol having a molecular weight of about 8,000 grams/mole and 400 grams of toluene. To this mixture was added 140 millimoles of sodium hydroxide (as an aqueous solution at 50% by weight sodium hydroxide). The flask was then heated to azeotropically distill off most of the water with stirring and nitrogen gas sparging. The conditions of distillation were such that about 1,000 ppm of water remained in the toluene solution. The solution was then cooled to 80° C. after which 90 millimoles of epichlorohydrin were added. The reaction mixture was then maintained at 80° C. until the epoxide titration reached approximately zero. (A 4.0 gram aliquot of the reaction mixture and 4 grams of tetraethylammonium bromide can be dissolved in 50 ml of glacial acetic acid and the resulting solution titrated with a 0.1036N $HClO_4$ in glacial acetic acid solution to a methyl violet end point for the amount of epoxide (epoxy titration). The reaction mixture was then neutralized to a substantially neutral pH (about pH 7) with aqueous hydrochloric acid. Butoxytriglycol (BTG) and water were added to give a clear yellow BTG/$H_2O$/product ratio of 1:2:2 by weight.

Example 5

The reaction was run according to the procedure outlined in Example 4 with the following exceptions. The amount of tridecyl alcohol ethoxylate was 80 millimoles, the amount of polyethylene glycol was 20 millimoles, and the amount of epichlorohydrin was 90 millimoles. In addition, 130 millimoles of sodium methoxide was used in place of the sodium hydroxide and then methanol was distilled off.

Example 6

The reaction was run according to the procedure outlined in Example 4 with the following exceptions. The amount of tridecyl alcohol ethoxylate was 85 millimoles, the amount of polyethylene glycol was 15 millimoles, and the amount of the sodium hydroxide was 130 millimoles.

Example 7

The reaction was run according to the procedure outlined in Example 5 with the following exceptions. The amount of tridecyl alcohol ethoxylate was 85 millimoles, the amount of polyethylene glycol was 15 millimoles, the amount of the sodium methoxide was 130 millimoles, and the amount of the epichlorohydrin was 115 millimoles.

Example 8

The reaction was run according to the procedure outlined in Example 5 with the following exceptions. The tridecyl alcohol ethoxylate was replaced with 80 millimoles of an ethoxylate of mixed alcohols having 12, 13, and 14 carbon atoms (nominal degree of ethoxylation of 100 moles of ethylene oxide per mole of alcohol) and the amount of polyethylene glycol was 20 millimoles.

Example 9

The reaction was run according to the procedure outlined in Example 5 with the following exceptions. The tridecyl alcohol ethoxylate was replaced with 80 millimoles of an ethoxylate of mixed alcohols having 8, 9, and 10 carbon atoms (nominal degree of ethoxylation of 100 moles of ethylene oxide per mole of alcohol) and the amount of polyethylene glycol was 20 millimoles.

Example 10

The reaction was run according to the procedure outlined in Example 5 with the following exceptions. The tridecyl alcohol ethoxylate was replaced with 80 millimoles of an nonyl phenol ethoxylate (nominal degree of ethoxylation of 100 moles of ethylene oxide per mole of alcohol) and the amount of polyethylene glycol was 20 millimoles.

Comparative Example 11

The reaction was run according to the procedure outlined in Example 5 with the following exceptions. The tridecyl alcohol ethoxylate was increased to 100 millimoles, no polyethylene glycol was added, the amount of sodium methoxide was 110 millimoles, and the amount of the epichlorohydrin was 80 millimoles.

Example 12

This example will illustrate the use of meta-alpha,alpha'-dichloromethyl benzene to introduce the meta-xylyl group into the structure of the molecule. To a 250 ml round bottom flask equipped with a stirrer, nitrogen inlet tube, and a distillation head were added 65 parts of tridecyl alcohol ethoxylate (nominal 100 ethyleneoxy units per mole of ethoxylate) and 18.5 parts by weight of polyethylene glycol having a molecular weight of about 8,000 grams/mole and 82 parts by weight of toluene (the mixture having a hydroxyl equivalent of 4.06. The mixture was heated to azeotropically distill off the water with stirring+$N_2$ sparge. After the water concentration is less than 50 ppm the mixture was cooled to 90° C. Sodium methoxide was added in an amount of 4.1 parts by weight of 25% sodium methoxide in methanol such that OH:NaOMe=1:1 based on the calculated hydroxyl value of the mixture. Heat was applied to distill off formed methanol (by distilling off about half of the initial weight of toluene from the flask). The reaction mixture was then refluxed for 1 hour. The flask was cooled to 80° C. and 1.64 parts by weight of meta-dichloromethyl benzene was added. After about ten minutes, an additional 0.2 parts by weight of meta-dichloromethyl benzene was added. The reaction mixture was maintained at 110° C. for about 1 hour then allowed to stand at room temperature for 16 hours before being reheated to 110° C. for about 2 more hours. The remaining toluene was then vacuum stripped. 76 parts by weight of distilled water was added to give a water white product which was cooled to room temperature.

Example 13

This example will illustrate the use of dimethyl maleate to introduce an ester linkage into the structure of the molecule. To a 250 ml round bottom flask equipped with a stirrer, nitrogen inlet tube, and a distillation head were added 86 parts of tridecyl alcohol ethoxylate (nominal 100 ethyleneoxy units per mole of ethoxylate) and 15.6 parts by weight of polyethylene glycol having a molecular weight of about 8,000 grams/mole and 20 parts by weight of toluene (the mixture having a hydroxyl equivalent of 1.8). To this mixture was added 1.8 parts by weight of dimethyl maleate. The mixture was then heated to 100° C. to azeotropically distill off any water with stirring+$N_2$ sparge. Then 0.1% of a commercial esterification catalyst, Fascat 4100, M&T Chemicals, Rahway, N.J., was and the mixture was heated to 170° C. for two hours.

This maleate ester was then converted to a sulfosuccinate ester by reaction with metabisulfite. To perform this reaction, the cooled reaction product from above was mixed with 100 parts by weight of deionized water and then 1.14 parts by weight of $Na_2 S_2O_5$ were added. The progress of the reaction was determined by titration with iodine and was quenched at about 92% conversion.

Table 1 shows the thickening ability of some of the compounds set forth above in a latex-based system, based on Rhoplex HG-74, Rhom & Haas Company, Philadelphia, Pa. The replicate of Example 13 is marked with an asterisk in Table 1, i.e. as Example 13*. This was the same material prepared in Example 10, but which was evaluated again after storage of the paint for one week at 50° C. This storage was found to degrade the performance of the compound of Example 13.

TABLE 1

Performance in High Gloss Latex Paint

| Example | % added | ICI | KU | F + L | Sag | Syneresis |
|---|---|---|---|---|---|---|
| 4 | 0.45 | 1.6 | 95 | 8 | 8 | No |
| 5 | 0.23 | 1.0 | 101 | 2 | 24 | — |
| 6 | 0.45 | 1.75 | 104 | 3 | 20 | No |
| 7 | 0.36 | 1.3 | 102 | 7 | 18 | No |
| 8 | 0.45 | 1.3 | 102 | 3 | 22 | No |
| 9 | 0.9 | 1.6 | 70 | 8 | 4 | No |
| 10 | 0.27 | 1.2 | 118 | — | — | — |
| 11 | 0.43 | 1.7 | 106 | 2 | 24 | Yes |
| 12 | 0.45 | 1.4 | 70 | — | — | — |
| 13 | 0.9 | 2.0 | 90 | — | — | — |
| 13* | 0.9 | 0.3 | <65 | — | — | — |
| Commercial Control | 0.45 | 1.6 | 96 | 8 | 8 | No |

What is claimed is:

1. A compound of the formula:

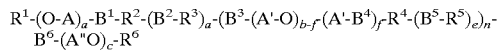

wherein:

R$^1$ and R$^6$ are monovalent hydrophobic groups independently selected from the group consisting of an aliphatic group, a substituted aliphatic group, an aromatic group, and a substituted aromatic group;

R$^2$ and R$^4$ are independently selected from the group consisting of alkanetriyl groups having from 2 to 10 carbon atoms and aralkylene groups having one benzenoid ring and from 1 to 10 aliphatic carbon atoms;

R$^3$ and R$^5$ are independently selected from hydrogen, lower alkyl and lower aralkyl;

B$^1$, B$^2$, B$^3$, B$^4$, B$^5$, and B$^6$ are linking groups independently selected from the group consisting of an oxygen atom, a carboxylate group, an amino group, and an amido group;

each of a, b, c, d, e, f, and n are integers, wherein each of a and C are independently any integer from greater than 20 to about 200; b is any integer from greater than 20 to about 450; d, e, and f are zero or 1; and n is any integer from 1 to about 5; and each of A, A', and A" is independently an ethylene, 1,2-propylene, 1,2-butylene unit or combinations thereof.

2. A compound of claim 1 wherein each of B$^1$, B$^2$, B$^3$, B$^4$, B$^5$, and B$^6$ are oxygen atoms.

3. A compound of claim 1 wherein each of B$^1$, B$^2$, B$^3$, B$^4$, B$^5$, and B$^6$ are carboxylate groups.

4. A compound of claim 1 wherein f is 1 and each of B$^1$, B$^2$, B$^3$, B$^4$, B$^5$, and B$^6$ are amino groups or amido groups having the formula —N(R)—, wherein R is selected from the group consisting of hydrogen, lower alkyl, and lower acyl.

5. A compound of claim 1 wherein d and e are each zero.

6. A compound of claim 1 wherein d and e are each 1 and $R^2$ and $R^4$ are both trivalent radicals selected from the group consisting of alkanetriyl groups having from 2 to 10 carbon atoms.

7. A compound of claim 1 wherein each of $R^1$ and $R^6$ is independently an aliphatic or aralkyl group having from 10 to about 30 carbon atoms.

8. A compound of claim 1 wherein each of d and e is 1 and each of $R^3$ and $R^5$ are hydrogen, methyl, or benzyl.

9. A compound of claim 1 wherein each of A, A', and A" are ethylene.

10. A compound of claim 1 wherein each of a and c are independently from about 50 to about 150.

11. A compound of claim 1 wherein b is from about 90 to about 300.

12. A compound of claim 1 wherein n is 1.

13. A compound of claim 1 wherein $R^1$ and $R^6$ are the same and are selected from the group consisting of alkyl groups having from about 8 to about 15 carbon atoms and alkylphenyl groups wherein the alkyl groups have from about 6 to about 12 carbon atoms.

14. A compound of claim 1 wherein each of $R^1$ and $R^6$ is independently an aliphatic or aromatic radical having from 10 to about 30 carbon atoms; $R^2$ and $R^4$ are both alkanetriyl groups having from 2 to 10 carbon atoms; d and e are each 1; $R^3$ and $R^5$ are hydrogen, methyl or benzyl; f is zero; each of $B^1$–$B^6$ is an oxygen atom; each of A, A', and A" is ethylene; a and c are independently from about 50 to about 150; b is from about 150 to about 300; and n is 1.

15. A compound of claim 14 wherein $R^2$ and $R^4$ are both propanetriyl radicals.

16. A compound of claim 1 wherein each of $R^1$ and $R^6$ is independently an aliphatic or aromatic radical having from 10 to about 30 carbon atoms; d, e, and f are each zero; each of $B^1$–$B^6$ is an oxygen atom; each of A, A', and A" is ethylene; a and c are independently from about 50 to about 150; b is from about 150 to about 300; and n is 1.

17. A compound of claim 16 wherein $R^2$ and $R^4$ are both meta-xylyl radicals.

18. A compound of the formula:

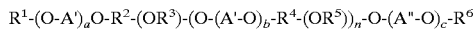

wherein
$R^1$, $R^2$, $R^3$, $R^4$, $R^5$, $R^6$, A, A', A", a, b, c, and n are as defined in claim 1.

19. A compound of claim 18 wherein $R^1$ and $R^6$ are the same and are selected from the group consisting of alkyl groups having from about 8 to about 15 carbon atoms and alkylphenyl groups wherein the alkyl groups have from about 6 to about 12 carbon atoms.

20. A compound of claim 18 wherein each of $R^1$ and $R^6$ is independently an aliphatic or aromatic radical having from 10 to about 30 carbon atoms; $R^2$ and $R^4$ are both trivalent radicals selected from the group consisting of alkanetriyl groups having from 2 to 10 carbon atoms; $R^3$ and $R^5$ are hydrogen, methyl or benzyl; each of A, A', and A" is ethylene; a and c are independently from about 50 to about 150; b is from about 150 to about 300; and n is 1.

21. A compound of claim 20 wherein $R^2$ and $R^4$ are both propanetriyl radicals.

22. A compound as claimed in claim 18 wherein each of $R^1$ and $R^6$ is independently an aliphatic or aralkyl radical having from 10 to about 30 carbon atoms; d and e are each zero; each of A, A', and A" is ethylene; a and c are independently from about 50 to about 150; b is from about 150 to about 300; and n is 1.

23. A compound of claim 22 wherein $R^2$ and $R^4$ are both meta-xylyl radicals.

24. A mixture of compounds of claim 1 of formula:

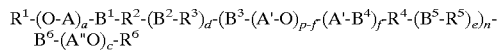

wherein:
$R^2$ and $R^4$ are alkanetriyl groups; and n is any integer or non-integer from 0.5 to 4.5.

25. A mixture of compounds of claim 24 wherein n is from 0.5 to 1.5.

26. An aqueous composition comprising water and a thickening-effective amount of a compound:

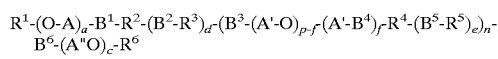

wherein:
$R^1$ and $R^5$ are monovalent hydrophobic groups independently selected from the group consisting of an aliphatic group, a substituted aliphatic group, an aromatic group, and a substituted aromatic group;

$R^2$ and $R^4$ are independently selected from the group consisting of alkanetiyl groups having from 2 to 10 carbon atoms and aralkylene groups having one benzenoid ring and from 1 to 10 aliphatic carbon atoms;

$R^3$ and $R^5$ are independently selected from hydrogen, lower alkyl and lower aralkyl;

$B^1$, $B^2$, $B^3$, $B^4$, $B^5$, and $B^6$ are linking groups independently selected from the group consisting of an oxygen atom, a carboxylate group, an amino group, and an amido group;

each of a, b, c, d, e, f, and n are integers, wherein each of a and c are independently any integer from greater than 20 to about 200; b is any integer from greater than 20 to about 450; d, e, and f are zero or 1; and n is any integer from 1 to about 5; and each of A, A', and A" is independently an ethylene, 1,2-propylene, 1,2-butylene unit or combinations thereof.

27. A latex composition comprising water, an emulsion polymer and from about 0.1% to about 10% by weight based emulsion polymer solids of a compound:

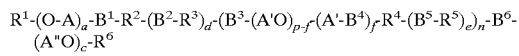

wherein:
$R^1$ and $R^6$ are monovalent hydrophobic groups independently selected from the group consisting of an aliphatic group, a substituted aliphatic group, an aromatic group, and a substituted aromatic group;

$R^2$ and $R^4$ are independently selected from the group consisting of alkanetriyl groups having from 2 to 10 carbon atoms and aralkylene groups having one benzenoid ring and from 1 to 10 aliphatic carbon atoms;

$R^3$ and $R^5$ are independently selected from hydrogen, lower alkyl and lower aralkyl;

$B^1$, $B^2$, $B^3$, $B^4$, $B^5$, and $B^6$ are linking groups independently selected from the group consisting of an oxygen atom, a carboxylate group, an amino group, and an amido group;

each of a, b, c, d, e, f, and n are integers, wherein each of a and c are independently any integer from greater than 20 to about 200; b is any integer from greater than 20 to about 450; d, e, and f are zero or 1; and n is any integer from 1 to about 5; and each of A, A', and A" is independently an ethylene, 1,2-propylene, 1,2-butylene unit or combinations thereof.

28. A compound of claim 1 wherein $R^2$ and $R^4$ are trivalent and the $B^2$ and $B^5$ groups are both oxygen.

29. The compound of claim 28 in which at least one of the $R^3$ and R5 groups is hydrogen.

30. The compound of claim 1 wherein an aqueous composition containing from about 35% to about 40% by weight thereof has a Brookfield viscosity in the range of from about 400 to about 20,000 cps.

31. A composition comprising at least one compound which is the reaction product of the following reactants:

$R^1$-(OA')$_a$-OH

HO-(A'O)$_b$-H

HO-(A"O)$_c$-R6

Y-$R^2$-(Y)$_d$Y"

in which $R^1$ and $R^6$ are monovalent hydrophobic groups independently selected from the group consisting of an aliphatic group, a substituted aliphatic group, an aromatic group, and a substituted aromatic group; $R^2$ is selected from the group consisting of alkanetriyl groups having from 2 to 10 carbon atoms and aralkylene groups having one benzenoid ring and from 1 to 10 aliphatic carbon atoms: each of a, b, c, and d are integers, wherein each of a and c is independently any integer from greater than 20 to about 200; b is any integer from greater than 20 to about 450; and d is zero or 1; each of A, A', and A" is independently an ethylene, 1,2-propylene, 1,2-butylene unit or combinations thereof; and Y, Y' and Y" are leaving groups.

32. The composition of claim 31 wherein the Y-$R^2$-(Y')$_d$Y" group is an epihalohydrin.

33. The composition of claim 32 wherein the epihalohydrin is epichlorohydrin.

34. The composition of claim 31 wherein the Y-$R^2$-(Y')$_d$Y" group is a precursor of an epihalohydrin having the formula X—$CH_2$—CH—(O$R^3$)—$CH_2$—X' where X' is a leaving group.

* * * * *